(12) United States Patent
Uchida

(10) Patent No.: US 9,784,610 B2
(45) Date of Patent: Oct. 10, 2017

(54) TERAHERTZ WAVE MEASURING DEVICE, MEASURING METHOD, AND MEASURING RIG

(71) Applicant: ARKRAY, Inc., Kyoto (JP)

(72) Inventor: Hirohisa Uchida, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days.

(21) Appl. No.: 14/965,972

(22) Filed: Dec. 11, 2015

(65) Prior Publication Data

US 2016/0169735 A1 Jun. 16, 2016

(30) Foreign Application Priority Data

Dec. 16, 2014 (JP) ................. 2014-254392

(51) Int. Cl.
| | |
|---|---|
| *G01J 1/08* | (2006.01) |
| *G01J 1/42* | (2006.01) |
| *G01J 1/02* | (2006.01) |
| *G01N 21/03* | (2006.01) |
| *G01N 21/35* | (2014.01) |
| *G01N 21/3577* | (2014.01) |
| *G01N 21/3581* | (2014.01) |
| *G01N 21/05* | (2006.01) |

(52) U.S. Cl.
CPC ............. *G01J 1/08* (2013.01); *G01J 1/0223* (2013.01); *G01J 1/42* (2013.01); *G01N 21/03* (2013.01); *G01N 21/3577* (2013.01); *G01N 21/3581* (2013.01); *G01N 2021/058* (2013.01)

(58) Field of Classification Search
CPC .. G01J 1/0223; G01J 1/08; G01J 1/42; G01N 2021/058; G01N 21/03; G01N 21/3577; G01N 21/3581
See application file for complete search history.

(56) References Cited

U.S. PATENT DOCUMENTS

| | | | |
|---|---|---|---|
| 2006/0255277 A1 | 11/2006 | Cole et al. | |
| 2012/0211659 A1 | 8/2012 | Kitamura et al. | |

FOREIGN PATENT DOCUMENTS

| | | |
|---|---|---|
| JP | 2007-248316 A | 9/2007 |
| JP | 2009-036693 | 2/2009 |
| JP | 2012-185151 A | 9/2012 |

OTHER PUBLICATIONS

Extended European Search Report issued in corresponding European Patent Application No. 15200071.7 dated Apr. 8, 2016.

*Primary Examiner* — Mark R Gaworecki
(74) *Attorney, Agent, or Firm* — Morgan, Lewis & Bockius LLP

(57) ABSTRACT

There is provided a terahertz wave measuring device including (1) a terahertz wave generation element that generates a terahertz wave by difference frequency generation based on excitation light that is incident to the terahertz wave generation element, the excitation light including a plurality of different wavelength components and being condensed so as to have a beam diameter of a predetermined size, (2) a structural body through which the terahertz wave is transmitted; and (3) a detector that detects an intensity of the terahertz wave that has been transmitted through the structural body, wherein the structural body includes a sample holder of a predetermined width that holds a sample, and the structural body is in close contact with or is joined to the terahertz wave generation element.

8 Claims, 17 Drawing Sheets

TERAHERTZ WAVE MEASURING DEVICE, MEASURING METHOD, AND MEASURING RIG

CROSS-REFERENCE TO RELATED APPLICATION

This application is claims priority under 35 USC 119 from Japanese Patent application No. 2014-254392 filed on Dec. 16, 2014, the disclosure of which is incorporated by reference herein.

BACKGROUND

Technical Field

The present disclosure relates to a terahertz wave measuring device, a terahertz wave measuring method, and a terahertz wave measuring rig.

Related Art

Conventionally, in general spectroscopic measurements and imaging using terahertz waves, emitted terahertz waves are guided so as to be incident on a sample, with a light source and the sample disposed separately from each other.

Moreover, terahertz wave characteristics measuring methods have been proposed that employ finely engineered structures, for example, micro electro mechanical systems (MEMS) and μ-total analysis systems (μ-TAS) (for example, see Japanese Patent Application Laid-Open (JP-A) No. 2012-185151). In such methods, terahertz waves are radiated onto a portion of a liquid solution that includes at least one type of substance subject to measurement and that has a thickness in the range of from 10 μm to 100 μm, such that the propagation direction is the thickness direction of the liquid solution. The spectroscopic characteristics of terahertz waves transmitted or reflected by that portion, or the intensity of terahertz waves of a particular frequency or particular wavelength, is measured.

A terahertz wave probe has also been proposed that includes a tube-shaped conductor having an opening in its leading end, that includes an emitting device for emitting electromagnetic waves from a position distanced from the opening at one out of a portion at the outside or a portion at the inside of the tube-shaped conductor, and that includes a detection device for detecting electromagnetic waves from a position distanced from the opening at the other portion (for example, see JP-A No. 2007-248316). This terahertz wave probe is configured such that detected electromagnetic waves respectively emitted and detected at the inside portion and the outside portion of the tube-shaped conductor, which has a size of the opening that is the wavelength of the electromagnetic waves or less, are coupled through the opening, and information about a specimen is acquired based on changes in the coupling of the electromagnetic waves through the opening when the specimen to be inspected is positioned facing the opening.

A near-field microscope has also been proposed including a laser device that emits a specific laser light, a light condensing lens that condenses the laser light to a specific light condensing point, and an electromagnetic wave emitting element that emits the electromagnetic waves in the vicinity of the light condensing point of the laser light and emits near-field light of the electromagnetic waves in the vicinity of the outer surface of the electromagnetic wave emitting element (for example, see JP-A No. 2009-036693). This near-field microscope further includes: a scanning mechanism that moves the sample or the laser light to make the near-field light approach the sample, and that converts the near-field light into propagating light using interaction between near-field light and sample; an electromagnetic wave detector that detects the propagating light reflected by the sample or scattered by the sample, and that acquires an image of the sample; and a half mirror that transmits laser light and that reflects electromagnetic waves toward the electromagnetic wave detector.

However, in the device described by JP-A No. 2012-185151, although the sample is loaded into a micro flow path and measurement of terahertz waves is performed for a minute region, it is, for example, difficult to measure terahertz waves for a minute region that requires spatial resolution exceeding the diffraction limit of the terahertz waves.

Moreover, in the device described by JP-A No. 2007-248316, it is necessary to include elements having complex structures in the construction of the light source and the probe, since the generated terahertz waves must be propagated by the probe that includes an opening no larger than the wavelength thereof.

Moreover, in the device described by JP-A No. 2009-036693, interaction between the near-field light and the sample is utilized, and a structure is required that uses a half mirror to reflect terahertz waves transmitted by the measurement sample or scattered by the measurement sample, and that detects the terahertz waves. In such a structure, the terahertz waves transmitted or reflected by the measurement sample, or scattered by the measurement sample, are detected after being transmitted through the terahertz wave generation element. However, in such cases, sometimes the terahertz waves pass through interfaces formed by each material due to reflection from the terahertz wave generation element or from the sample, or from the rear face of the sample, and are affected by absorption and reflection of the terahertz waves in the terahertz wave generation element, the sample, and in free space, leading to the need to perform complex calculation or data processing in order to accurately measure the characteristics of the measurement target.

SUMMARY

The present disclosure provides a terahertz wave measuring device, measurement method, and measuring rig enabling measurement of terahertz waves for a minute region using a configuration that is both simple, and not affected by absorption of a terahertz wave generation element.

Solution to Problem

A first aspect of the present disclosure is a terahertz wave measuring device including: a terahertz wave generation element that generates a terahertz wave by difference frequency generation based on excitation light that is incident to the terahertz wave generation element, the excitation light including a plurality of different wavelength components and being condensed so as to have a beam diameter of a predetermined size, a structural body through which the terahertz wave is transmitted, and a detector that detects an intensity of the terahertz wave that has been transmitted through the structural body, wherein the structural body includes a sample holder of a predetermined width that holds a sample, and the structural body is in close contact with or is joined to the terahertz wave generation element.

According to the first aspect, the terahertz wave having the beam diameter of the predetermined size is incident to the sample held by the sample holder of the predetermined width on the structural body that is in close contact with or is joined to the terahertz wave generation element, and the terahertz wave that has been transmitted through the structural body is detected, thus enabling measurement of terahertz waves in a minute region using a simple configuration not affected by absorption of the terahertz wave generation element.

A second aspect of the present disclosure is the terahertz wave measuring device of the first aspect, wherein the predetermined size of the beam diameter of the excitation light is shorter than the width of the sample holder.

This enables the beam diameter of the terahertz wave incident to the sample to be constrained very close to the beam diameter of the excitation light, thereby enabling measurement of terahertz waves in a more minute region.

A third aspect of the present disclosure is the terahertz wave measuring device of the first or second aspect, further including: a moving section that moves a light path of the excitation light, or moves the structural body, such that an incident position of the excitation light is moved in one dimension or in two dimensions with respect to the terahertz wave generation element, wherein the detector detects the intensity of the terahertz wave according to the incident position of the excitation light with respect to the terahertz wave generation element.

This enables imaging of the characteristics of the structural body corresponding to the incident position of the excitation light with respect to the terahertz wave generation element, namely, the intensity of the terahertz wave reflecting the shape of the region in which the sample is held.

A fourth aspect of the present disclosure is the terahertz wave measuring device of any one of the first to the third aspect, wherein the terahertz wave generation element is a non-linear optical crystal that achieves phase matching in difference frequency generation.

A fifth aspect of the present disclosure is the terahertz wave measuring device of the fourth aspect, wherein the non-linear optical crystal is an organic non-linear optical crystal that is a DAST crystal, a DASC crystal, or an OH1 crystal.

A sixth aspect of the present disclosure is a terahertz wave measuring method including condensing excitation light having light of a plurality of different wavelength components so as to have a beam diameter of a predetermined size, having the condensed excitation light be incident to a terahertz wave generation element so as to generate a terahertz wave by difference frequency generation based on the condensed excitation light, transmitting the terahertz wave through a structural body that includes a sample holder of a predetermined width that holds a sample, the structural body being in close contact with or being joined to the terahertz wave generation element, and detecting an intensity of the terahertz wave that has been transmitted through the structural body.

A seventh aspect of the present disclosure is the terahertz wave measurement method of the sixth aspect, further including: comparing an intensity of the terahertz wave detected for a sample to be measured against an intensity of the terahertz wave detected in advance for a known sample of known concentration, and measuring the concentration of the sample to be measured.

An eighth aspect of the present disclosure is the terahertz wave measurement method of the sixth aspect, further including: comparing an intensity of the terahertz wave detected for a sample to be measured against respective intensities of terahertz waves detected in advance for known samples, and identifying the sample to be measured.

A ninth aspect of the present disclosure is a terahertz wave measuring rig including: a terahertz wave generation element that generates a terahertz wave by difference frequency generation based on excitation light, including light of a plurality of different wavelength components that is condensed so as to have a beam diameter of a predetermined size, being incident to the terahertz wave generation element, and a structural body through which the terahertz wave is transmitted, wherein the structural body includes a sample holder of a predetermined width that holds a sample, and the structural body is in close contact with or is joined to the terahertz wave generation element.

As explained above, the terahertz wave generation device, measurement method, and measuring rig of each aspect of the present disclosure enable measurement of terahertz waves in a minute region using a configuration that is both simple, and not affected by absorption of a terahertz wave generation element.

BRIEF DESCRIPTION OF THE DRAWINGS

Exemplary embodiments of the present disclosure will be described in detail based in the following figures, wherein.

DETAILED DESCRIPTION

Detailed explanation follows regarding an exemplary embodiment according to a terahertz wave measuring device of technology disclosed herein, with reference to the drawings.

First Exemplary Embodiment

Figure 1:
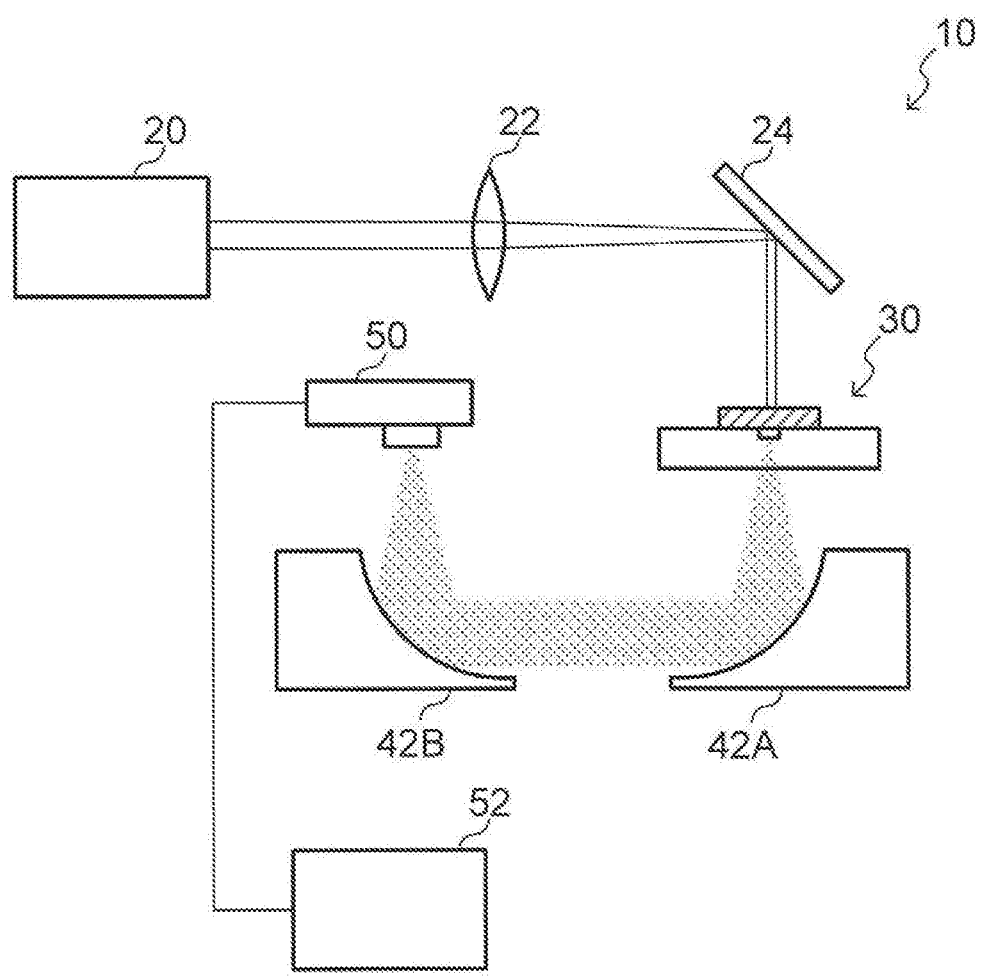
FIG. 1 is a schematic diagram illustrating a configuration of a terahertz wave measuring device according to a first exemplary embodiment.

As illustrated in FIG. 1, a terahertz wave measuring device 10 according to a first exemplary embodiment is configured including an excitation light emitting device 20 that emits excitation light, a condenser lens 22 that condenses the excitation light, a mirror 24 that guides the focused excitation light to a terahertz wave generator 30, the terahertz wave generator 30 that makes the terahertz waves generated by the excitation light incident to a sample, a pair of parabolic mirrors 42A, 42B that guide the terahertz waves transmitted through the terahertz wave generator 30, a detection device 50 that detects the intensity of the guided terahertz waves, and a processor 52 that processes terahertz wave detection results.

The excitation light emitting device 20 may employ, for example, a KTP parametric oscillator (KTP-OPO) or a BBO parametric oscillator (BBO-OPO) that emits excitation light of two different wavelengths. For example, the KTP-OPO is configured including a pumped light source, and two potassium titanyl phosphate ($KTiOPO_4$: KTP) crystals. The pumped light source is a light source that outputs pumped light that acts as the basis for emission of excitation light of two wavelengths in the KTP-OPO, and may employ, for example, a second harmonic wave of an Nd:YAG laser (wavelength: 532 nm, pulse width: 24 ns, repetition frequency: 50 Hz).

Each KTP crystal is mounted to a rotating stage such that the incidence angles of pumped light incident to the crystals can be independently adjusted. The frequency of excitation light emitted from the KTP-OPO can be changed by changing the incidence angle of the pumped light to the KTP crystals. For example, the excitation light emitting device 20 may be caused to emit excitation light having the two wavelengths $\lambda 1=1300$ nm and $\lambda 2=1308$ nm.

The condenser lens 22 condenses the excitation light such that the beam diameter of the excitation light in the terahertz wave generator 30 is smaller than the measurement region of the sample onto which the terahertz waves are incident (the width of a micro flow path 32C, explained later, in the present exemplary embodiment). For example, the beam diameter of the excitation light may be constrained to 100 μm by the condenser lens 22.

Figure 2:
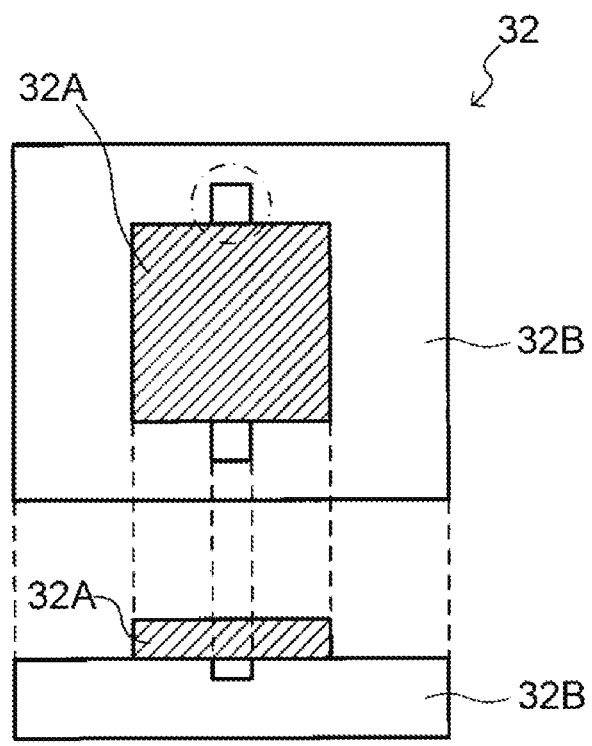
FIG. 2 is a top view and a side view schematically illustrating a measuring rig of the first exemplary embodiment.

The terahertz wave generator 30 generates terahertz waves using incident excitation light, and is also a sample stage on which a sample subject to measurement, and to which the generated terahertz waves are incident, is placed. The sample is loaded into a measuring rig 32 such as that illustrated in FIG. 2, for example. FIG. 2 is a top view and a side view of the measuring rig 32. The measuring rig 32 is configured such that a terahertz wave generation element 32A and a finely engineered structure 32B are in close contact with each other.

An organic optical crystal, such as a 4-dimethylamino-N-methyl-4-stilbazolium tosylate (DAST) crystal, a 4-dimethylamino-N-methyl-4-stilbazolium-p-chlorobenzene sulfonate (DASC) crystal, or a 2-(3-(4-hydroxystyryl)-5,5-dimethylcyclohex-2-enylidene) malononitrile (OH1) crystal, may be employed as the terahertz wave generation element 32A. Moreover, an inorganic optical crystal, such as gallium phosphate ($GaPO_4$), gallium arsenide (GaAs), or lithium niobate ($LiNobO_3$), may be employed therefor.

Figure 3:
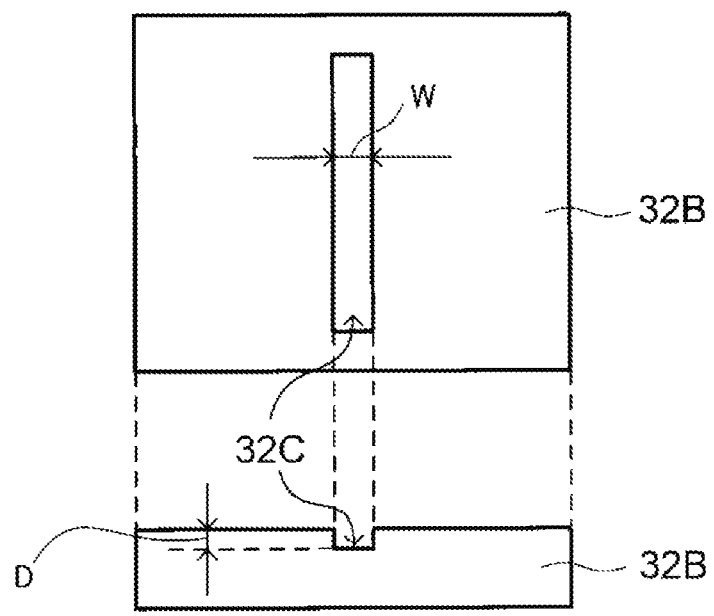
FIG. 3 is a top view and a side view schematically illustrating of a finely engineered structure of the first exemplary embodiment.

A material having high transmittance to terahertz waves, such as an annular olefin based polymer, polydimethylsiloxane (PDMS), an ultra-high molecular weight polyethylene (UHMW-E), or a high resistance silicon wafer, may be employed as the material of the finely engineered structure 32B. Moreover, as illustrated in FIG. 3, a micro flow path 32C is formed to the finely engineered structure 32B by fine processing. The micro flow path 32C is, for example, a groove having a predetermined width W (for example, W=500 μm) and a predetermined depth of D (for example, D=100 μm). The micro flow path 32C holds the sample. In a state in which the terahertz wave generation element 32A is in close contact with the finely engineered structure 32B, the terahertz wave generation element 32A forms a cap on the micro flow path 32C, and the sample is loaded into a space portion formed by the micro flow path 32C and the terahertz wave generation element 32A.

Note that the depth of the micro flow path 32C is preferably in a range of from 10 μm to 100 μm. When the depth of the micro flow path 32C is less than 10 μm, the transmittance to terahertz waves is excessive and distinguishing spectroscopic characteristics can no longer be obtained. The operation of loading the sample into the micro flow path 32C also becomes difficult. When the depth the micro flow path 32C exceeds 100 μm, the effect of absorption of terahertz waves by water molecules acting as the solvent becomes too great, and spectroscopic characteristics of substances in the solution can no longer be measured. It is accordingly appropriate to set the depth of the micro flow path 32C within a range of from 10 μm to 100 μm.

Moreover, the width of the micro flow path 32C is preferably greater than the beam diameter of the terahertz waves incident to the sample in accordance with the principles of the present exemplary embodiment described below. As described below, the present exemplary embodiment is configured such that the beam diameter of the terahertz waves incident to the sample is substantially equal to the beam diameter of the excitation light, and therefore the width of the micro flow path 32C is preferably the beam diameter of the excitation light or greater.

Next, explanation follows regarding principles of the present exemplary embodiment.

Figure 4:
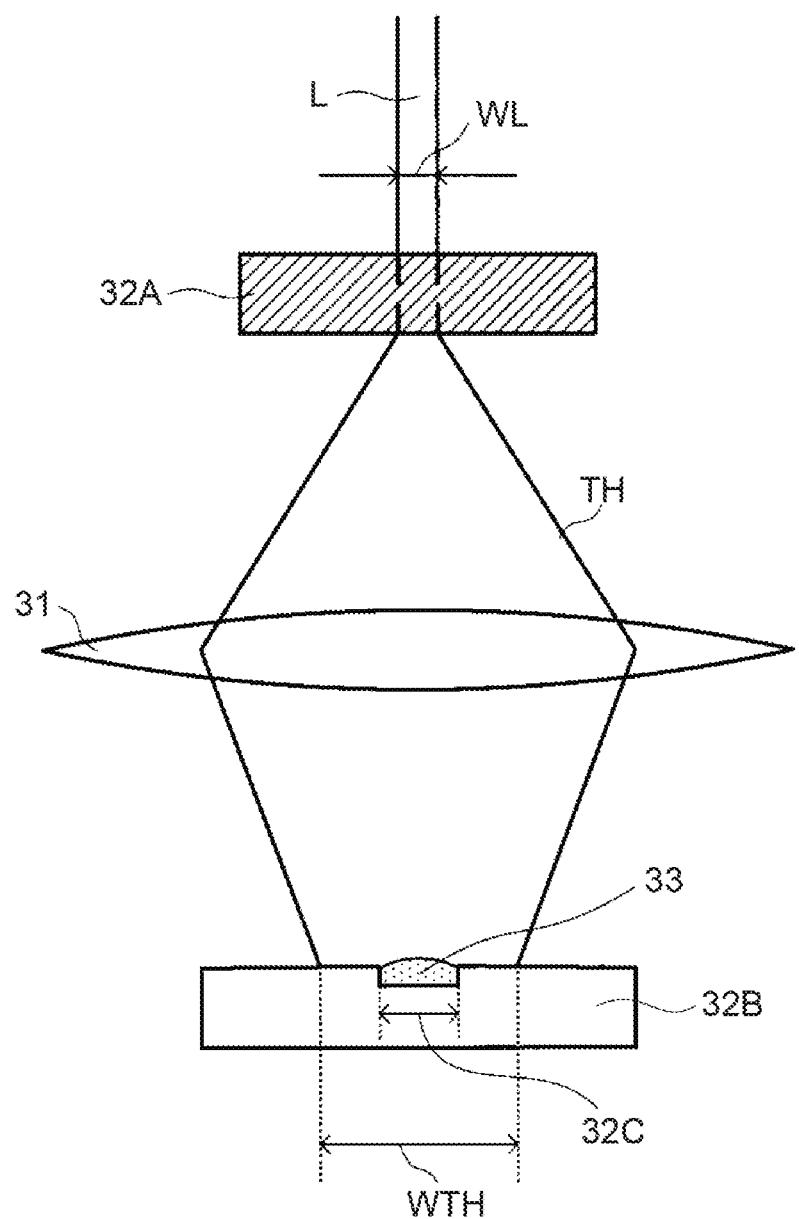
FIG. 4 is a diagram for explaining principles of embodiments of technology disclosed herein.

FIG. 4 schematically illustrates a state in which excitation light is incident to a terahertz wave generation element, and terahertz waves generated from the terahertz wave generation element are condensed so as to be incident to the sample. As illustrated in FIG. 4, the terahertz waves generated from the terahertz wave generation element are scattered as they progress along the optical path. It is not possible to condense a diameter WTH of the terahertz wave at incidence to the wavelength of the generated terahertz waves or less when incident to the sample when condensing using a condenser 31 such as a condenser lens, a parabolic mirror, or the like, due to the effect of the diffraction limit of the terahertz waves. Namely, the spatial resolution of the terahertz waves, which have been scattered then condensed, when the terahertz waves are incident to the sample to the sample, cannot be made smaller than the wavelength of the generated terahertz waves.

Accordingly, as illustrated in FIG. 4, in cases in which the width of the micro flow path that holds the sample 33 is smaller than the wavelength of the terahertz waves TH, terahertz waves TH are also incident to areas other than the sample 33. In such cases, a significant amount of terahertz waves that have not been transmitted through the sample 33, namely, noise components, are included in terahertz waves detected at a later stage.

Note that it is conceivable to make the width of the micro flow path greater than the beam diameter of the terahertz waves when they are incident in order to prevent terahertz waves from being incident to areas other than the sample. However, when the width of the micro flow path is made large, the amount of sample required for the measurement increased by the same extent. In cases in which, for example, the substance has a high value or has a high rarity value, preparation of large amounts is difficult, and it is accordingly desirable to set the width of the micro flow path small so as to enable measurement of small amounts of sample.

As illustrated in FIG. 4, although terahertz waves from the terahertz wave generation element are scattered after generation, the beam diameter of the terahertz waves immediately after generation is substantially the same size as the beam diameter WL of the excitation light L that was incident to the terahertz wave generation element. Namely, terahertz waves having a minute diameter can be obtained by constraining the beam diameter WL of the excitation light L to a minute size, as long as just after generation from the terahertz wave generation element.

Figure 5:
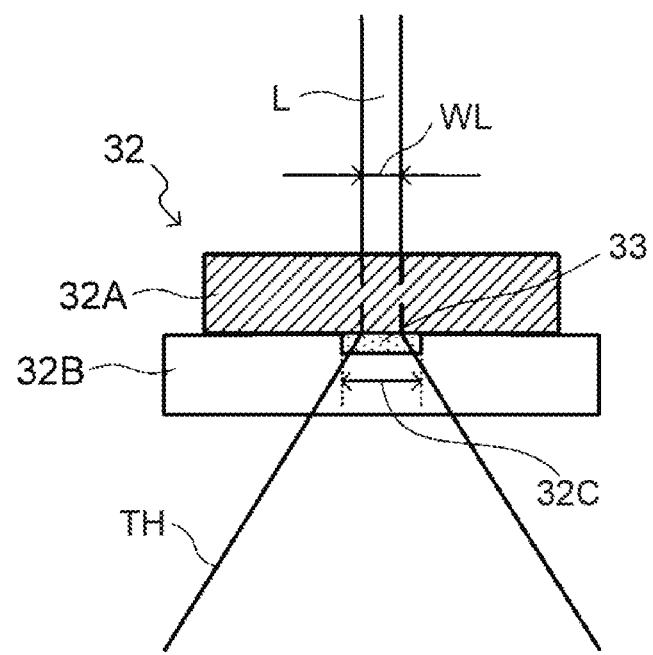
FIG. 5 is a diagram for explaining principles of embodiments of technology disclosed herein.

In accordance with the above principles, in the present exemplary embodiment, as illustrated in FIG. 5, by placing the terahertz wave generation element 32A and the finely engineered structure 32B in close contact with each other, in addition to constraining the beam diameter of the excitation light to a size smaller than the width of the micro flow path 32C into which a sample is loaded, a configuration is achieved in which terahertz waves, having substantially the same diameter as the beam diameter of the excitation light are incident, just after being generated from the terahertz wave generation element 32A, to a sample loaded into the micro flow path 32C.

Moreover, following the above principles enables terahertz waves to be measured at a spatial resolution exceeding the diffraction limit of the terahertz waves by setting the width of the finely engineered structure 32B and the beam diameter of the excitation light smaller than the wavelength of the terahertz waves that were generated. For example, when 1.41 THz terahertz waves have been generated as a wavelength difference between two wavelengths of excitation light, the wavelength of the terahertz waves becomes 212.6 µm. Making the beam diameter of the excitation light a beam diameter of 212.6 µm, which is the wavelength of the terahertz waves to be generated, or less, results in a spatial resolution that exceeds the diffraction limit of the terahertz waves being achievable.

Figure 6:
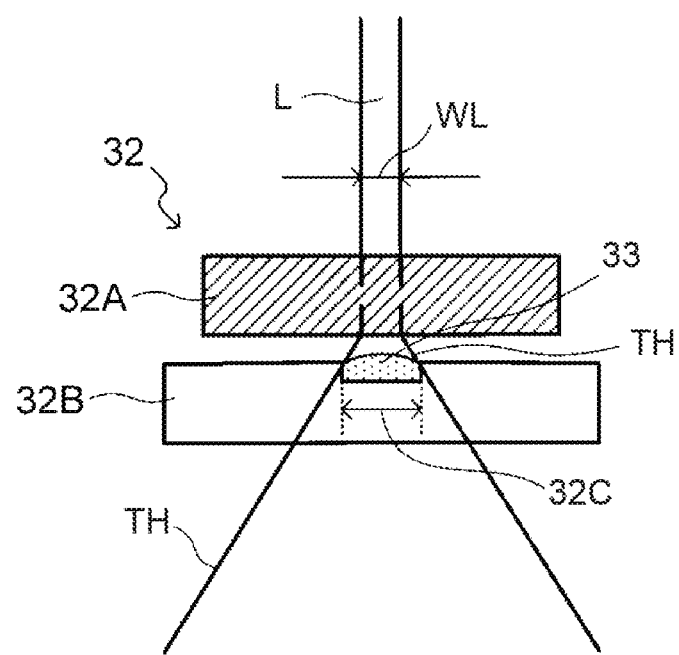
FIG. 6 is a diagram for explaining principles of embodiments of technology disclosed herein.

Note that explanation has been given regarding a case in the present exemplary embodiment in which the terahertz wave generation element 32A and the finely engineered structure 32B are placed in close contact with each other; however, the terahertz wave generation element 32A and the finely engineered structure 32B may be disposed so as to be separated from each other within a range following the above principles. Namely, as illustrated in FIG. 6, the terahertz wave generation element 32A and the finely engineered structure 32B may disposed at a separation such that the terahertz waves TH generated from the terahertz wave generation element 32A are incident before the beam diameter of the terahertz waves has been scattered as far as the width of the micro flow path 32C.

Figure 7:
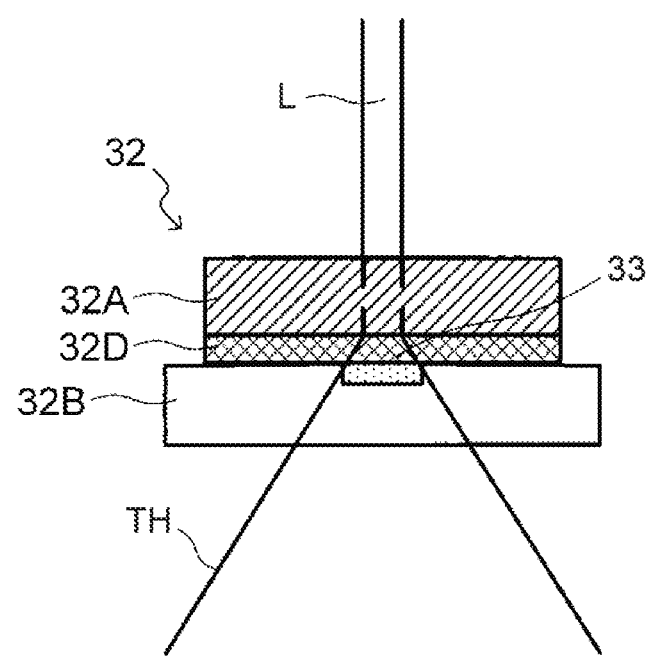
FIG. 7 is a schematic diagram illustrating an example of a configuration in which a sheet is provided between a terahertz wave generation element and a finely engineered structure.

In such cases, as illustrated in FIG. 7, it is possible to provide a sheet 32D between the terahertz wave generation element 32A and the finely engineered structure 32B. This is an effective measure in cases in which, for example, there is a concern that the terahertz wave generation element may dissolve in the sample. The material of the sheet 32D may be the same material as that of the finely engineered structure 32B, such as PDMS, provided that the material is a material having transmittance to terahertz waves.

Moreover, there is no particular limitation to the method by which the terahertz wave generation element 32A and the finely engineered structure 32B are placed in close contact with each other. For example, the characteristics of the material (for example, silicon) of the finely engineered structure 32B may be utilized, and the terahertz wave generation element 32A may be simply placed on the finely engineered structure 32B, or alternatively the terahertz wave generation element 32A may be gently pressed against the finely engineered structure 32B after being placed thereon.

Moreover, the measuring rig 32 may be configured such that the terahertz wave generation element 32A is joined to the finely engineered structure 32B. For example, when performing fixing after adding another fluid for forming the micro flow path 32C to a predetermined fluid as the process of forming the micro flow path 32C in the finely engineered structure 32B, the measuring rig 32 may be formed with the terahertz wave generation element 32A and the finely engineered structure 32B joined together by placing the terahertz wave generation element 32A in close contact with the finely engineered structure 32B and fixing. Moreover, the measuring rig 32 may be formed with the terahertz wave generation element 32A and the finely engineered structure 32B joined together by placing the terahertz wave generation element 32A in close contact with the finely engineered structure 32B with the terahertz wave generation element 32A in a molten state, and then cooling.

Note that when the terahertz wave generation element 32A and the finely engineered structure 32B are placed in closed contact or joined together, the polarization direction of the excitation light and the optical axis of the crystal axis of the terahertz wave generation element 32A may be aligned in consideration of orientation when the measuring rig 32 is disposed facing the terahertz wave generator 30.

The parabolic mirrors 42A, 42B, after condensing the terahertz waves that have been transmitted through the finely engineered structure 32B into parallel light, guide the terahertz waves to the detection device 50. The detection device 50 detects the intensity of the terahertz waves that have been transmitted through the finely engineered structure 32B, and outputs the intensity to the processor 52.

The processor 52 includes a computer that includes a CPU, ROM, RAM, and the like, and a display section such as a display. In the processor 52, for example, the intensity of terahertz waves detected by the detection device 50 is acquired, and converted into optical characteristics expressed as a ratio to the transmittance of water, which serves as a reference. Then, the converted optical characteristics of the terahertz waves are compared against pre-stored optical characteristics expressed as a ratio of a known substance to water, and the substance subject to measurement is identified. The optical characteristics expressed as a ratio to water for the known substance are obtained in advance using the above method for measuring the optical characteristics thereof. More specifically, a solution of the known substance is loaded into the micro flow path 32C of the measuring rig 32, and optical characteristics of terahertz waves are measured. Then, using the optical characteristics of water measured similarly, the optical characteristics for the known substance are obtained as expressed by the ratio of the transmittance of the known substance to the transmittance of water. The processor 52 displays the identification results on the display section.

Note that the processing performed by the processor 52 is not limited to identification of the substance subject to measurement. The optical characteristics of the measured terahertz waves may be output as they are, and the concentration of the substance subject to measurement may be measured using the optical characteristics of terahertz waves pre-measured for a known sample at a known concentration.

Next, explanation follows regarding operation of the terahertz wave measuring device 10 according to the first exemplary embodiment. The method of measuring terahertz waves performed by the terahertz wave measuring device 10 of the first exemplary embodiment is an example of a terahertz wave measuring method of technology disclosed herein.

First, the sample is loaded into the micro flow path 32C of the measuring rig 32. Loading of the sample can be performed by injecting through a location of the micro flow path 32C that is not blocked by the terahertz wave generation element 32A (for example, the location indicated by the dot-dashed circle illustrated in FIG. 2). Moreover, this may be performed by capping with the terahertz wave generation element 32A in a state in which the sample is held in the micro flow path 32C of the finely engineered structure 32B before placing the terahertz wave generation element 32A in close contact. The measuring rig 32 loaded with the sample is then disposed on the terahertz wave generator 30 so as to face the surface of the terahertz wave generation element 32A at the side at which the excitation light is incident.

Next, excitation light having two different wavelengths (for example, $\lambda 1 = 1300$ nm, $\lambda 2 = 1308$ nm) is emitted from the excitation light emitting device 20. The emitted excitation light is condensed to a predetermined beam diameter by the condenser lens 22 (for example, 100 µm), is reflected by the mirror 24, and is incident to the terahertz wave generation element 32A of the measuring rig 32.

In the terahertz wave generation element 32A, terahertz waves corresponding to the frequency difference in the excitation light are generated by difference frequency generation based on the incident excitation light. The generated terahertz waves are incident to the sample loaded into the micro flow path 32C of the finely engineered structure 32B. The terahertz wave generation element 32A and the finely engineered structure 32B are in close contact with each other, such that terahertz waves that have just been generated from the terahertz wave generation element 32A, namely, terahertz waves having a beam diameter substantially the same as the beam diameter of the excitation light, are incident to the sample. In the present exemplary embodiment, the beam diameter of the excitation light is smaller than the width of the micro flow path 32C, so as to enable the terahertz waves to be incident to the sample, without including regions other than the sample.

The terahertz waves that have been transmitted through the sample are then guided to the detection device 50 by the parabolic mirrors 42A, 42B. In the detection device 50, the intensity of the guided terahertz waves is detected, and the detection result is output to the processor 52.

In the processor 52, the optical characteristics of the terahertz waves are measured from the intensity of the terahertz waves detected by the detection device 50, processing such as identification of the substance subject to measured is performed, and the processing result is output.

As explained above, according to the terahertz wave measuring device and the terahertz wave measurement method according to the first exemplary embodiment, the terahertz wave generation element and the finely engineered structure provided with the micro flow path into which the sample is loaded are in close contact with each other, and excitation light is incident with a beam diameter smaller than the width of the micro flow path. Measurement of the terahertz waves for a minute region is thereby possible since terahertz waves having a beam diameter substantially the same as the beam diameter of the excitation light are incident to the sample.

Moreover, setting the width of the micro flow path and the beam diameter of the excitation light so as to be smaller than the wavelength of the terahertz waves to be generated enables measurement of terahertz waves at a spatial resolution exceeding the diffraction limit of the terahertz waves.

Thus, since it is possible to measure terahertz waves for a minute region, such as by measuring at a spatial resolution exceeding the diffraction limit of the terahertz waves, the width of the micro flow path to hold the sample can be made finer and measurement of terahertz waves with an extremely small sample is possible, for example in cases in which the sample subject to measurement has a high value or has a high rarity value.

Moreover, since the terahertz waves to be generated from the terahertz wave generation element are not near-field light, they can be transmitted through the sample, and there is no need to consider absorption of the terahertz waves from the terahertz wave generation element that arising when terahertz waves that have been reflected by a sample are detected, enabling terahertz waves to be detected using a simple configuration.

Moreover, there is no light path for the terahertz waves propagating through free space between the terahertz wave generation element and the sample, enabling propagation loss of the terahertz waves to be reduced. Moreover, there is no need for a structure that condenses terahertz waves generated from the terahertz wave generation element and guides the terahertz waves to the sample, enabling the overall configuration of the device to be simplified.

Second Exemplary Embodiment

Next, explanation follows regarding a second exemplary embodiment. Note that in a terahertz wave measuring device according to the second exemplary embodiment, configuration similar to that of the terahertz wave measuring device 10 according to the first exemplary embodiment is allocated the same reference numerals and detailed explanation thereof is omitted.

Figure 8:
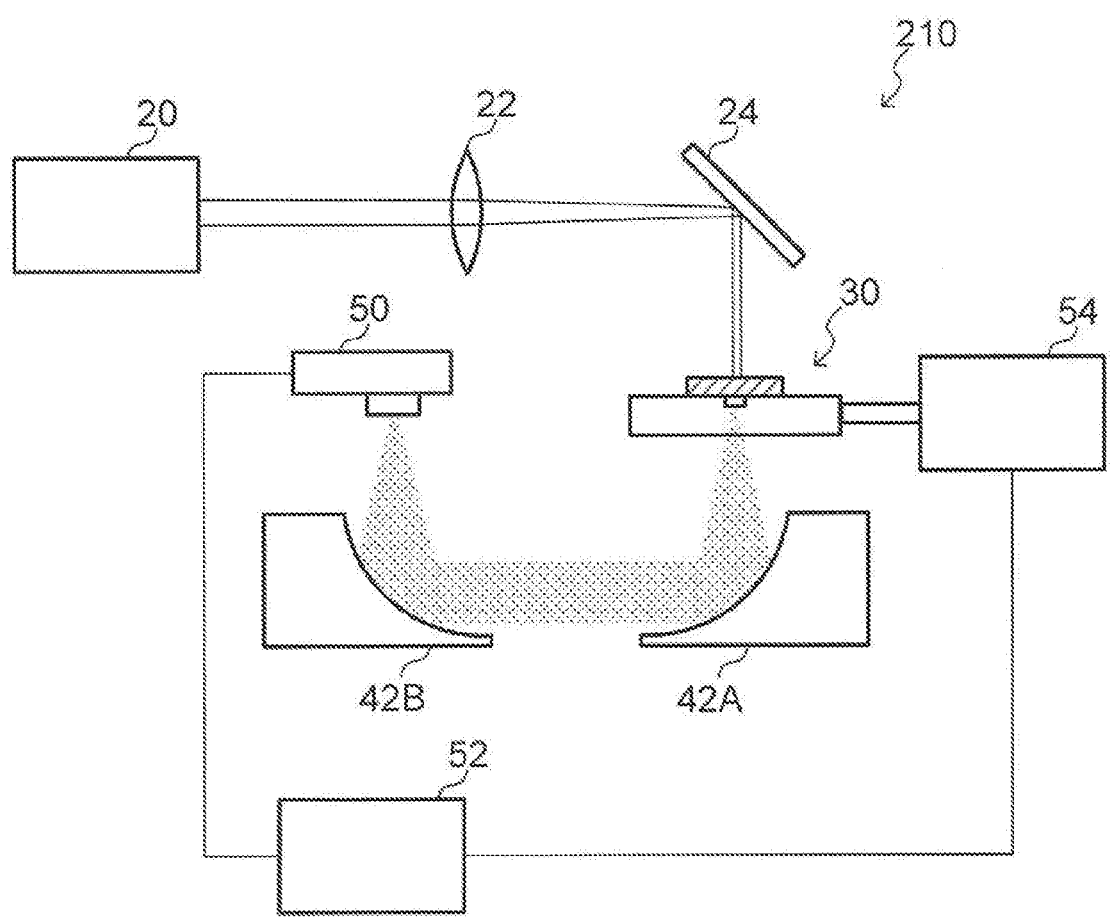
FIG. 8 is a schematic diagram illustrating a configuration of a terahertz wave measuring device according to a second exemplary embodiment.

As illustrated in FIG. 8, a terahertz wave measuring device 210 according to the second exemplary embodiment is configured including a moving mechanism 54 that moves the measuring rig 32 disposed in the terahertz wave generator 30, in addition to the configuration of the terahertz wave measuring device 10 according to the first exemplary embodiment.

The moving mechanism 54 may be any mechanism that moves the measuring rig 32 such that the incident position of the excitation light moves in one dimension or two dimensions with respect to the terahertz wave generation element 32A of the measuring rig 32 under instruction from the processor 52. For example, an XYZ three-axis moving stage may be employed as the moving mechanism 54.

Figure 9:
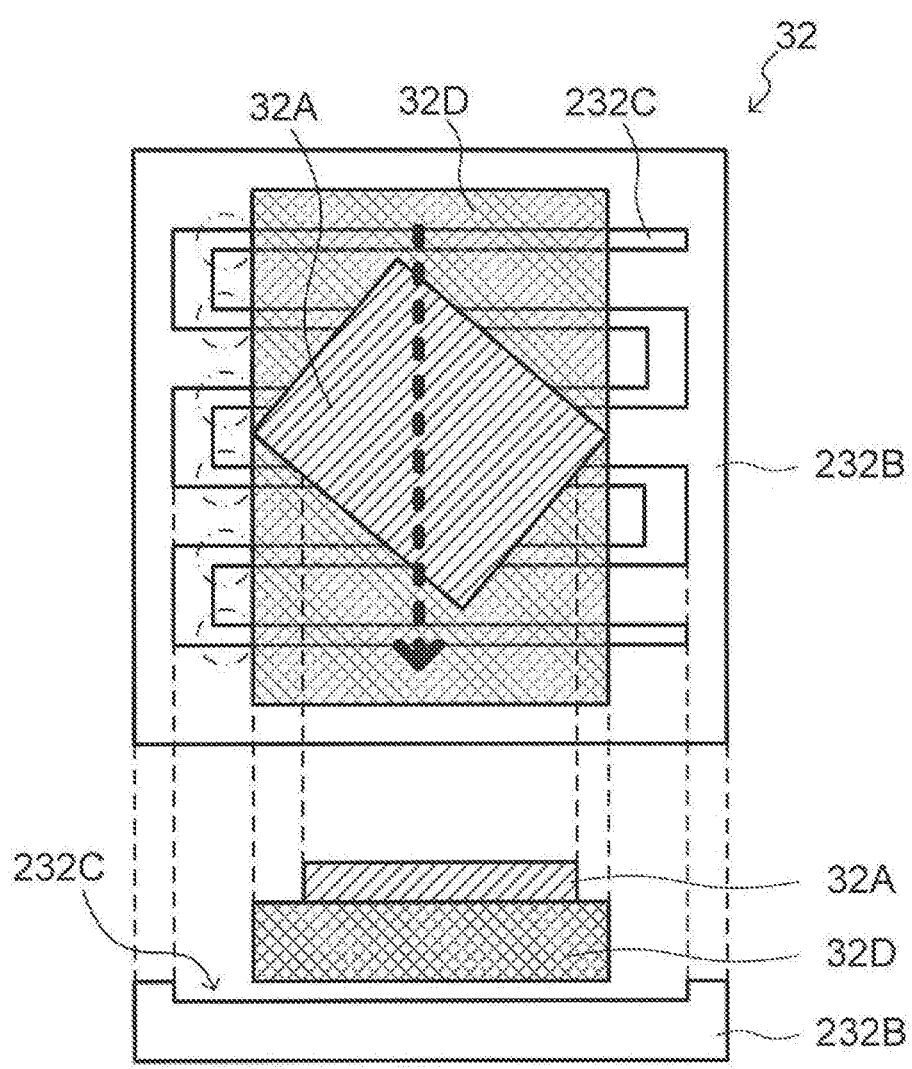
FIG. 9 is a top view and a side view schematically illustrating a measuring rig of the second exemplary embodiment.
Figure 10:
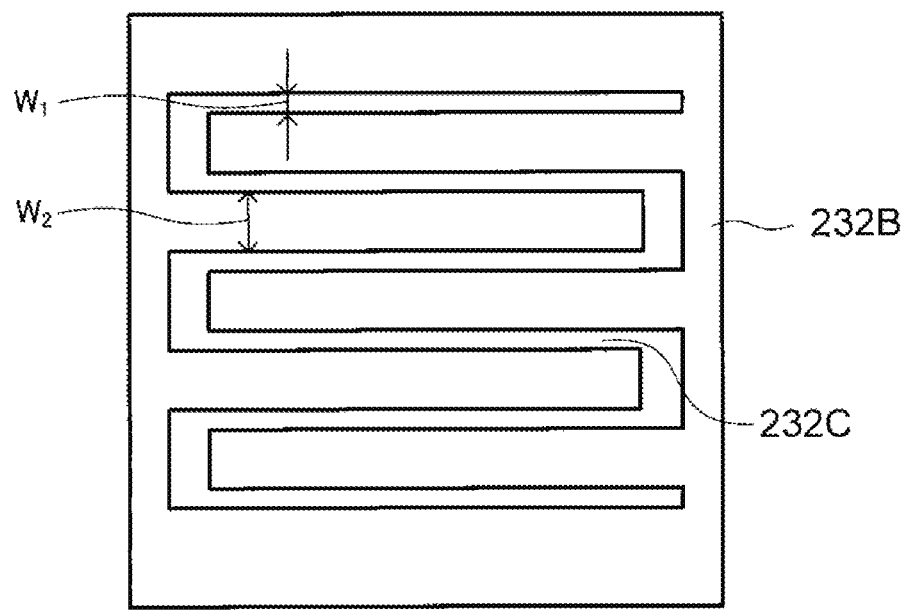
FIG. 10 is a top view schematically illustrating a finely engineered structure of the second exemplary embodiment.

FIG. 9 is a top view and a side view of the measuring rig 32 of the second exemplary embodiment. The measuring rig 32 of the second exemplary embodiment is configured such that the sheet 32D is placed in close contact on a finely engineered structure 232B, and the terahertz wave generation element 32A is placed in close contact thereon. Moreover, as illustrated in FIG. 10, the finely engineered structure 232B includes a micro flow path 232C shaped differently to that of the first exemplary embodiment. In the example of FIG. 10, plural flow paths (six in the example of FIG. 10) having a predetermined width of $W_1$ (for example, $W_1$=500 μm) are disposed parallel to one another at a predetermined flow path separation $W_2$ (for example, $W_2$=1.2 mm), with the end portions of each of the flow paths alternately joined to adjacent flow paths so as to give a meandering shape. The terahertz wave generation element 32A is disposed on the finely engineered structure 232B provided with the thus configured micro flow path 232C, and as illustrated by the dashed arrow in FIG. 9, for example, the measuring rig 32 is moved by the moving mechanism 54 so as to move the incident position of the excitation light, thereby enabling imaging to be performed of the intensity of the terahertz waves according to the incident position of the excitation light.

Note that the shape of the micro flow path 232C provided to the finely engineered structure 232B is not limited to the example illustrated in FIG. 10. Any shape may be employed in which plural regions for holding the sample are provided, and that is capable of detecting the respective intensities of the terahertz waves transmitted through the plural measurement locations, which depend on the incident position of the excitation light, with moving the incident position of the excitation light. Moreover, it is sufficient for the width $W_1$ of each of the flow paths corresponding to each of the regions of the micro flow path 232C to be greater than the beam diameter of the terahertz waves incident to the sample, similarly to the width W of the flow path of the first exemplary embodiment.

Next, explanation follows regarding operation of the terahertz wave measuring device 210 according to the second exemplary embodiment. The method of measuring terahertz waves performed by the terahertz wave measuring device 210 of the second exemplary embodiment is an example of a terahertz wave measurement method of technology disclosed herein. Note that detailed explanation is omitted for portions similar to the operation of the terahertz wave measuring device 10 according to the first exemplary embodiment.

First, a sample is loaded into the micro flow path 232C of the measuring rig 32. Loading of the sample can be performed by pouring in through a location of the micro flow path 232C not blocked by the terahertz wave generation element 32A (for example, the locations indicated by the dot-dashed circles in FIG. 9). The measuring rig 32 loaded with the sample is then held by the moving mechanism 54.

Next, excitation light is emitted from the excitation light emitting device 20. The emitted excitation light is condensed to a predetermined beam diameter (for example, 100 μm) by the condenser lens 22, is reflected by the mirror 24, and is incident to the terahertz wave generation element 32A of the measuring rig 32.

Accompanying incidence of the excitation light to the terahertz wave generation element 32A, the processor 52 instructs the moving mechanism 54 to move the measuring rig 32 along a predetermined direction. The moving mechanism 54 moves the held measuring rig 32 according to the instructions from the processor 52. The incident position of excitation light is thereby moved with respect to the terahertz wave generation element 32A.

When the excitation light is incident, terahertz waves are generated from the terahertz wave generation element 32A, and terahertz waves that have just been generated are incident to a position of the finely engineered structure 232B corresponding to the incident position of the excitation light. When the incident position of the excitation light corresponds to the position of the micro flow path 232C of the finely engineered structure 232B, terahertz waves that have just been generated are incident to the sample.

Terahertz waves transmitted through respective positions of the finely engineered structure 232B including the sample are then guided to the detection device 50 by the parabolic mirrors 42A, 42B. In the detection device 50, the intensity of the guided terahertz waves is detected, and the detection result is output to the processor 52.

In the processor 52, imaging is performed of the intensity of terahertz waves that depends on the incident position of the excitation light, based on information instructed to the moving mechanism 54 and the intensity of the terahertz waves acquired from the detection device 50, and the imaging result is output.

Figure 11:
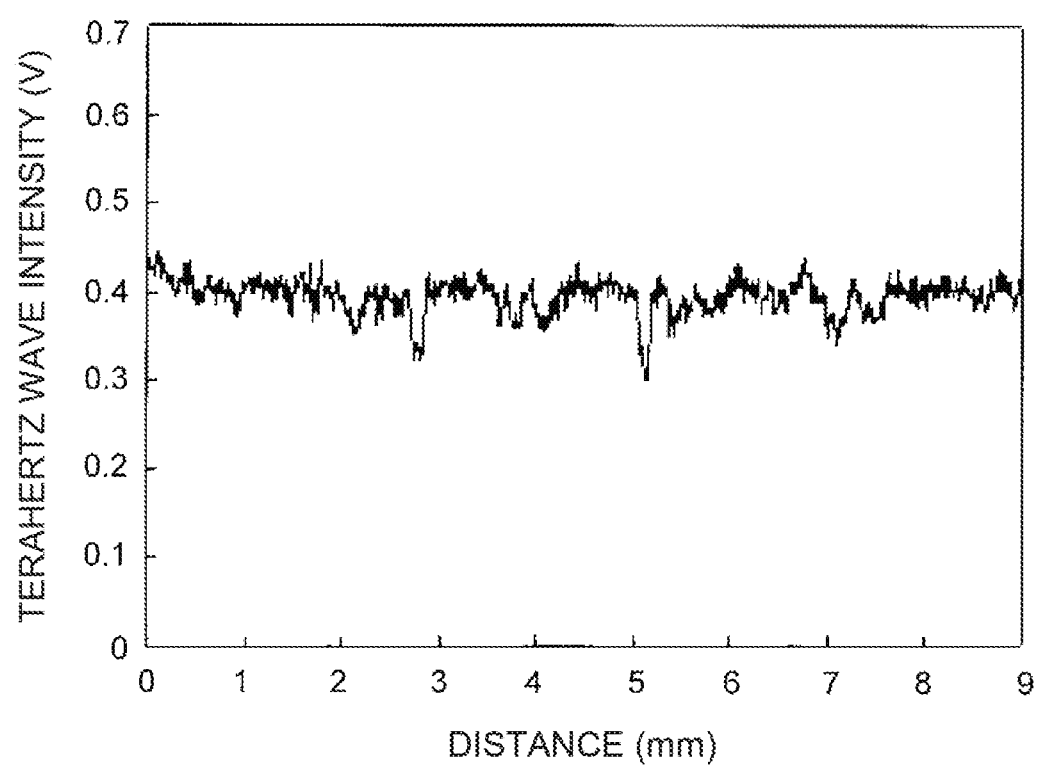
FIG. 11 is a diagram illustrating an example of imaging results in a case of an empty flow path.
Figure 12:
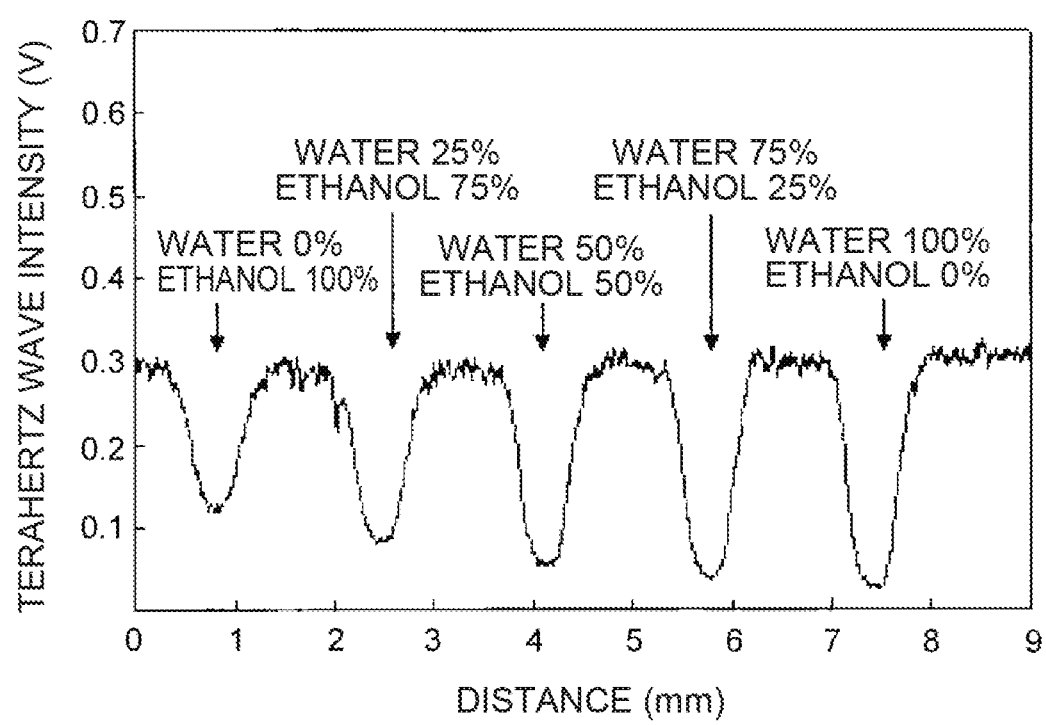
FIG. 12 is a diagram illustrating an example of imaging results in a case of ethanol/water solutions of different concentrations being loaded into respective flow paths.

FIG. 11 illustrates the imaging result when nothing is loaded into the micro flow path 232C (an empty flow path). FIG. 12 illustrates the imaging result when ethanol solutions of different concentrations are loaded into the respective flow paths of the micro flow path 232C, and the excitation light is scanned along the dashed arrow illustrated in FIG. 9. The horizontal axis of FIG. 11 and FIG. 12 indicates the distance along the scanning direction with reference to the initial incident position of the excitation light, and the vertical axis indicates the intensity of the terahertz waves detected when the excitation light is incident to the position corresponding to the distance on the horizontal axis. As illustrated in FIG. 11, terahertz waves are detected without being influenced by the shape of the micro flow path 232C when the flow path is empty. On the other hand, as illustrated in FIG. 12, imaging results are obtained that reflect the characteristics of the micro flow path 232C formed by the finely engineered structure 232B when ethanol solutions having different concentrations are loaded into the respective flow paths. Moreover, imaging results are obtained in which the terahertz wave intensities at positions corresponding to the respective flow paths reflect the concentration of the ethanol solution loaded into that flow path.

Thus, as illustrated in FIG. 12, imaging of the intensity of the terahertz waves of the sample can be performed for plural samples simultaneously by loading solutions of different concentrations, or by loading different samples, into each of the flow paths. Moreover, for samples in which a reaction is progressing, the state of progress in a sample reaction can be imaged by loading samples with different states of progress into each of the flow paths.

As explained above, according to the terahertz wave measuring device and the terahertz wave measurement method of the second exemplary embodiment, in addition to the first exemplary embodiment, imaging results can be obtained that reflect characteristics of the micro flow path 232C formed in the finely engineered structure 232B, namely, the shape of the region in which the sample is held, by moving the incident position of the excitation light with respect to the terahertz wave generation element. Moreover, imaging results can be obtained that reflect characteristics such as concentration and type of the sample held the position corresponding to the incident position of the excitation light.

Note that explanation has been given in the second exemplary embodiment regarding a case in which the incident position of the excitation light is scanned with respect to the terahertz wave generation element by moving the measuring rig; however, there is no limitation thereto. For example, configuration may be made such that the mirror 24 is a movable type, the reflection direction of the excitation light is freely modifiable, and the excitation light is scanned with respect to the fixed measuring rig.

Moreover, explanation has been given in the second exemplary embodiment regarding a case in which the incident position of the excitation light is scanned in one dimension with respect to the terahertz wave generation element; however, configuration may be made so as to scan in two dimensions. This would enable the shape of the micro flow path to be ascertained based on imaging results such as imaging results in cases in which the shape of the micro flow path is not known, namely, the positions at which the sample is present are not known.

EXAMPLES

Explanation follows regarding examples related to comparative verification testing for explanation of technology disclosed herein.

Figure 13:
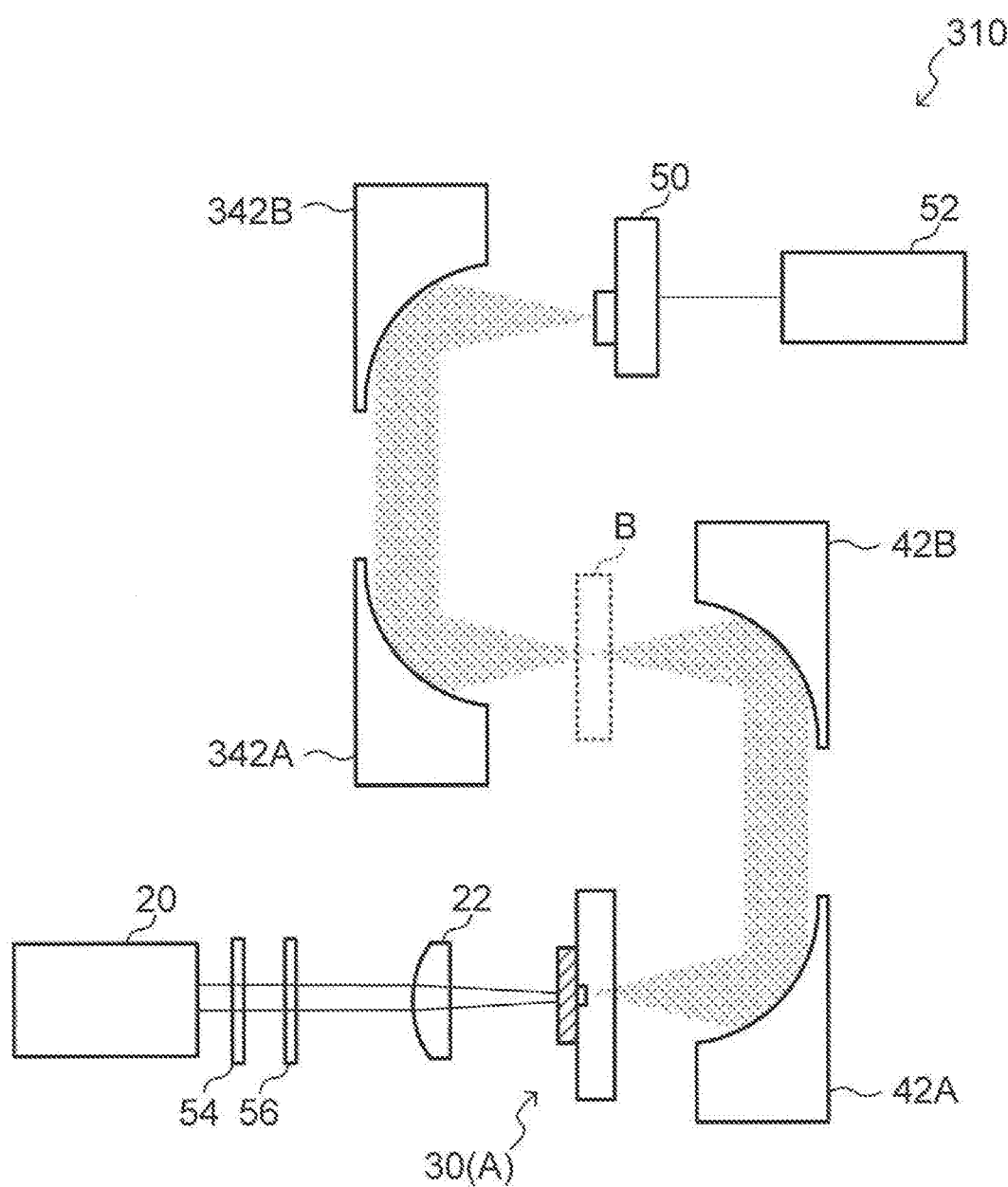
FIG. 13 is a schematic diagram illustrating a configuration of an example for comparative verification.

FIG. 13 illustrates a schematic configuration of a terahertz wave measuring device 310 according to an example employed in the comparative verification testing. Note that configuration similar to the configurations of the terahertz wave measuring device 10 according to the first exemplary embodiment and the terahertz wave measuring device 210 according to the second exemplary embodiment are allocated the same reference numerals, and detailed explanation thereof is omitted.

As illustrated in FIG. 13, the terahertz wave measuring device 310 according to the examples includes an excitation light emitting device 20, a ½ wavelength plate 54, an attenuator 56, a condenser lens 22, a terahertz wave generator 30, two pairs of parabolic mirrors 42A, 42B and 342A, 342B, a detector 50, and a processor 52.

A BBO-OPO that pumps light of the third harmonic wave of an Nd:YAG laser having a wavelength of 355 nm, output of 400 mJ, a pulse width of 8 ns, and a repetition frequency of 10 Hz, was employed as the excitation light emitting device 20. Two wavelengths of light, having wavelength $\lambda 1 = 1255$ nm, wavelength $\lambda 2 = 1268.8$ nm (when at 2.6 THz) or wavelength $\lambda 2 = 1278$ nm (when at 4.3 THz), and output 0.6 mJ, were output by the BBO-OPO.

A convex lens having a focal distance of 40 mm was employed as the condenser lens 22. A DAST crystal was employed as the terahertz wave generation element 32A. The parabolic mirrors 42A, 42B, 342A employed had a focal distance of 76.2 mm, and the parabolic mirror 342B had a focal distance of 50.8 mm. A pyro detector manufactured by PLUXi was employed as the detection device 50.

Similarly to in the first and second exemplary embodiment, the terahertz wave generator 30 generated terahertz waves due to incidence of excitation light, and was a sample stage on which the sample subject to measurement was placed with the generated terahertz waves incident thereto. Similarly to in the first and the second exemplary embodiment, the sample is held in the measuring rig 32 having the terahertz wave generation element 32A and the finely engineered structure 32B placed in close contact with each other. In the present exemplary embodiment, the sample stage implemented by the terahertz wave generator 30 is referred to as "sample stage A".

Moreover, the terahertz wave measuring device 310 includes a sample stage B for comparison against technology disclosed herein, placed at the condensing position of the terahertz waves reflected by the parabolic mirror 42B. A sample holder is disposed on the sample stage B, and terahertz waves generated from the terahertz wave generation element 32A disposed at a position on the sample stage A are guided to the parabolic mirrors 42A, 42B, and are incident to the sample holder.

The measuring rig 32 disposed on the sample stage A had the shape of the measuring rig (FIG. 2 and FIG. 3) employed in the first exemplary embodiment, and therefore employed a finely engineered structure 32B having a width W of 100 μm, a depth D of 100 μm, and a thickness of 200 μm.

The sample holder disposed on the sample stage B employed only a portion of the finely engineered structure 32B of the measuring rig 32 described above. When the sample was disposed on the sample stage B and the terahertz wave intensity was measured, the terahertz waves, which were generated in a state in which the finely engineered structure 32B had been removed from the measuring rig 32 of the terahertz wave generator 30 and only the terahertz wave generation element 32A remained, were guided by the pair of parabolic mirrors 42A, 42B, and made incident to the sample holder on which the sample stage B was disposed.

Note that although the sample stages A and B are both omitted from illustration in FIG. 13, the sample stages A and B were moved by the moving mechanism 54 so as to move the incident position of the excitation light or the terahertz waves in one dimension.

Using the terahertz wave measuring device 310 according to the example configured as described above, a 75 μm diameter metal wire (silver wire), employed as a measurement sample 33, was disposed in the micro flow path to compare the shielding rate for terahertz waves between the sample stages A and B.

Figure 14:
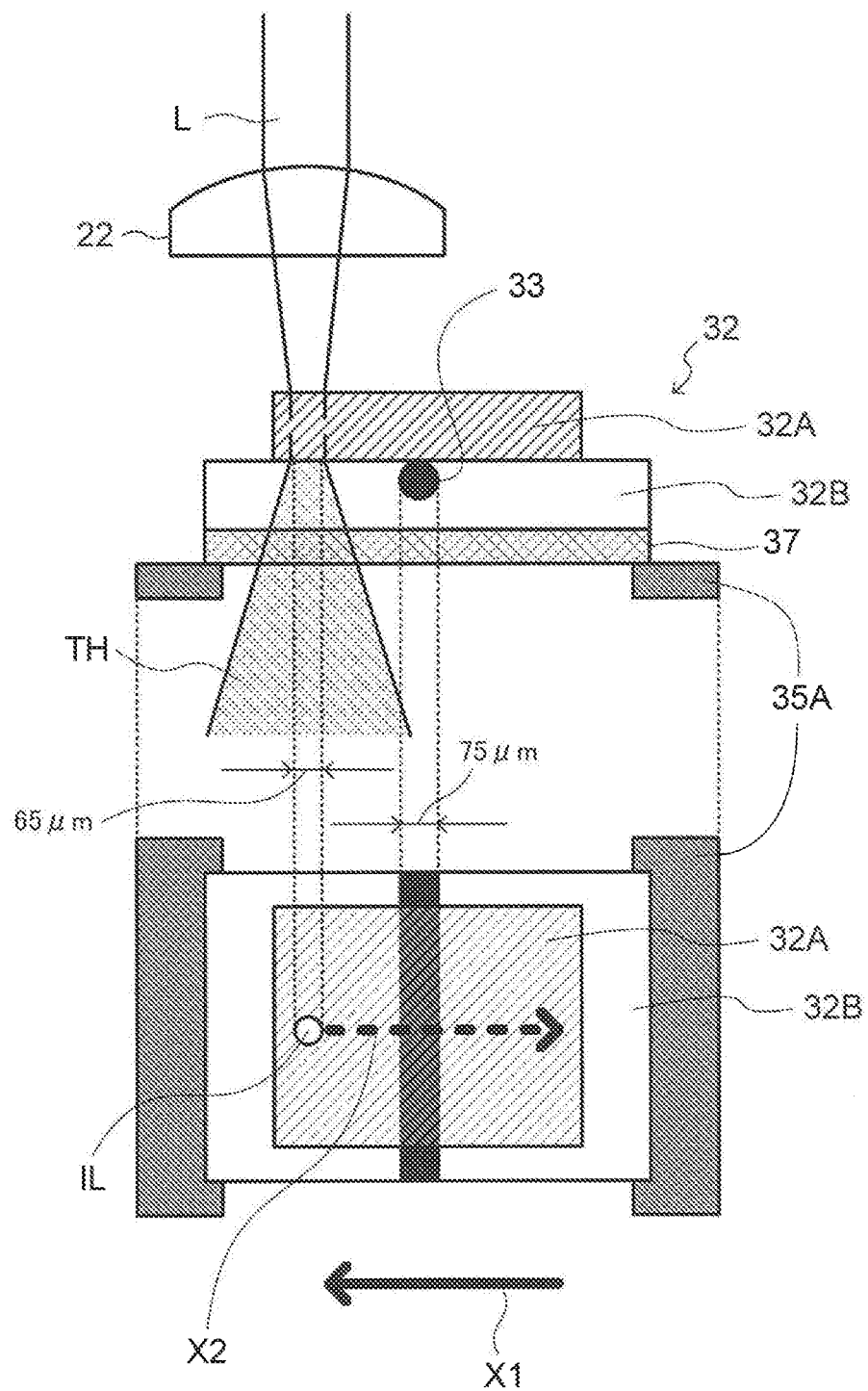
FIG. 14 is a schematic diagram of a sample stage A of an example.

FIG. 14 is a side view and a top view that schematically illustrate the sample stage A. Excitation light L condensed by the condenser lens 22 is incident to the terahertz wave generation element 32A side face of the measuring rig 32 through a TEFLON (registered trademark) sheet 37 placed on a knife-edge device stage 35A. In the present example, the beam diameter WL of the excitation light L when incident to the terahertz wave generation element 32A was 65 μm. The incident position IL of the excitation light L was moved in the direction of the dashed arrow X2 in FIG. 14 by moving the sample stage A in the direction of the solid arrow X1 in FIG. 14. One dimensional imaging results were thereby acquired for the intensity of terahertz waves that had been generated by the incidence of the excitation light and transmitted through the measuring rig 32 and the sample 33.

Figure 15:
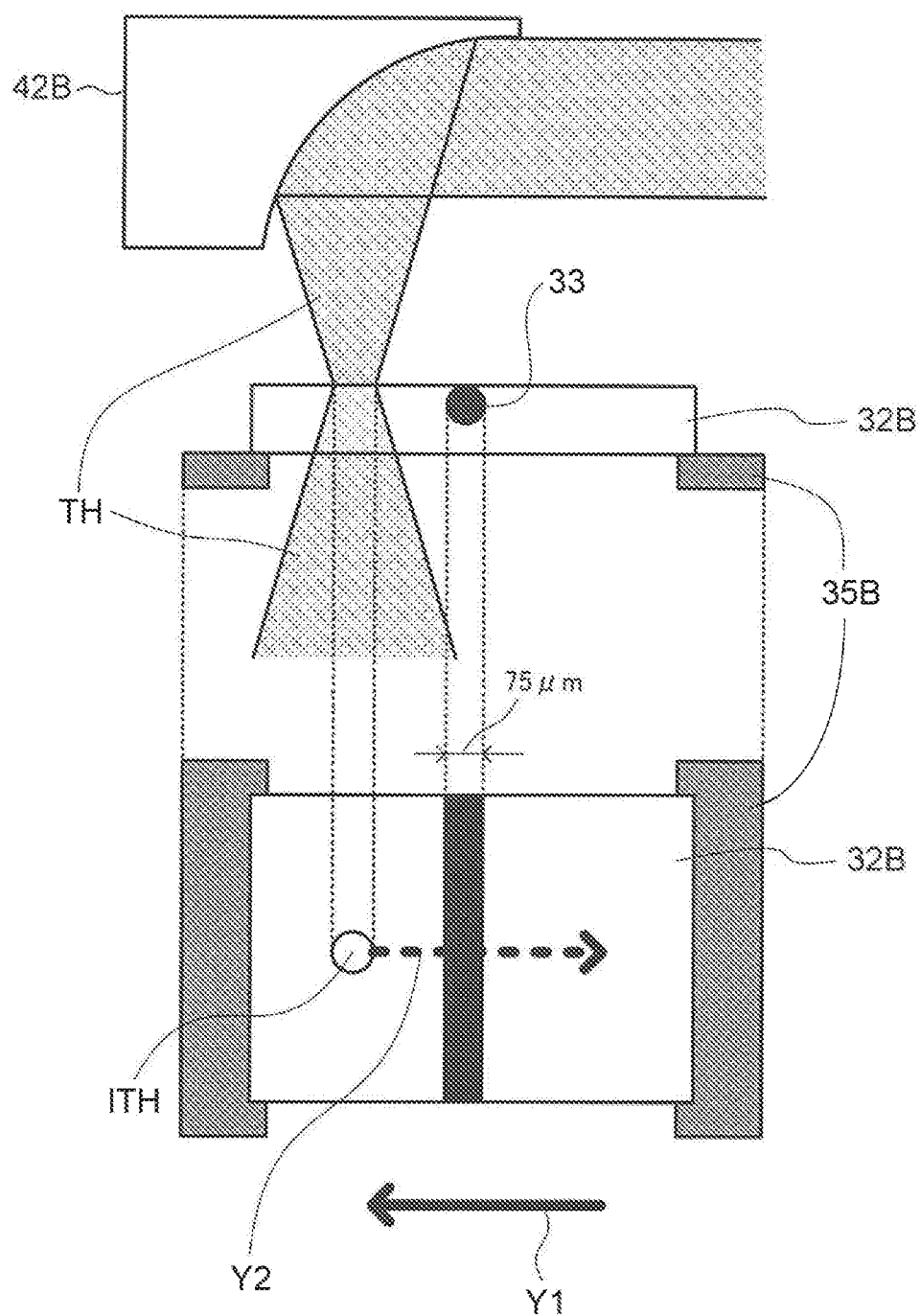
FIG. 15 is a schematic diagram of a sample stage B of an example.

FIG. 15 is a side view and a top view that schematically illustrate a sample stage B. Terahertz waves TH that have been generated by the terahertz wave generation element 32A disposed at a position on the terahertz wave generator 30, are guided by the pair of parabolic mirrors 42A, 42B to a sample holder (the finely engineered structure 32B) disposed on a knife-edge device stage 35B. The incident position ITH of the terahertz waves TH is moved in the direction of the dashed arrow Y2 in FIG. 15 by moving the sample stage B in the direction of the solid arrow Y1 in FIG. 15. One dimensional imaging results of intensities of terahertz waves TH that have been transmitted through the sample holder and the sample 33 are thereby acquired. A beam diameter of the terahertz wave TH at incidence to the finely engineered structure 32B is equal to the wavelength of the generated terahertz wave TH or more.

Figure 16:
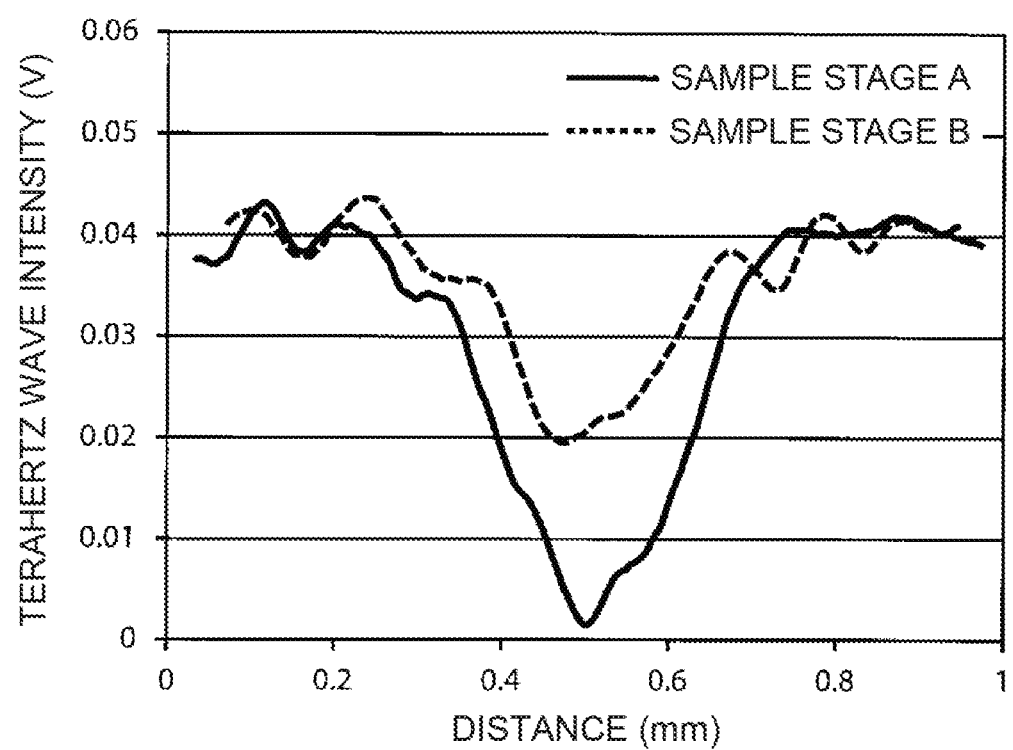
FIG. 16 is a diagram illustrating an example of imaging results of an example.
Figure 17:
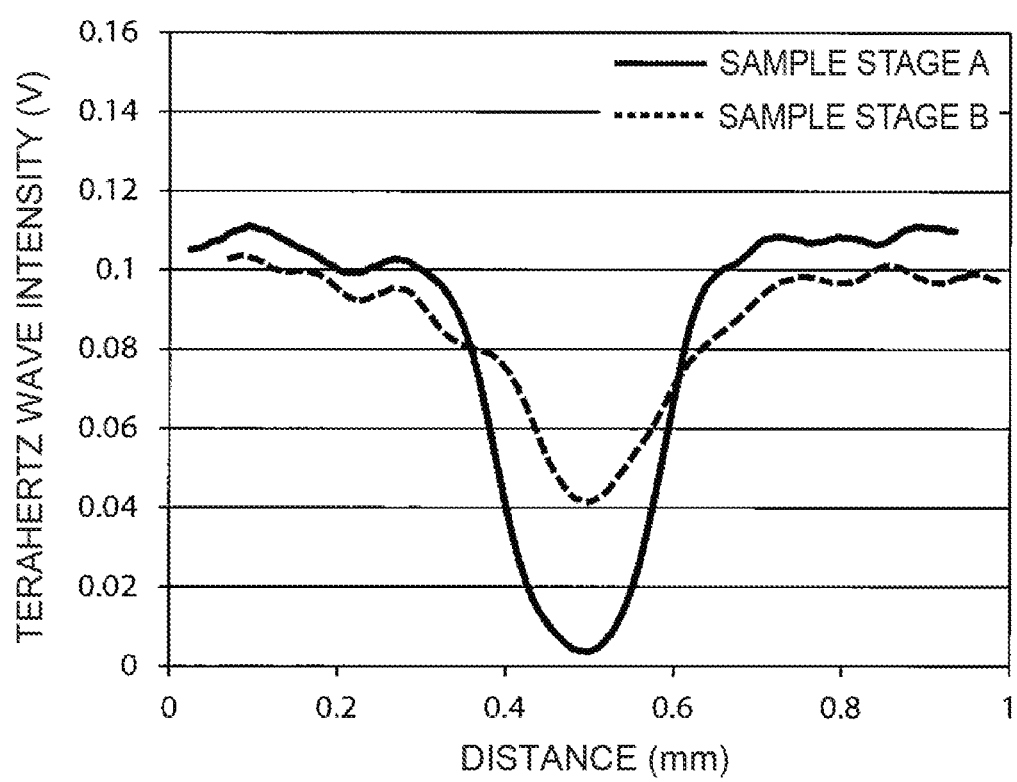
FIG. 17 is a diagram illustrating an example of imaging results of an example.

FIG. 16 illustrates one dimensional imaging results of intensities of terahertz waves that have been transmitted through the respective sample stages A and B, in a case in which the wavelength $\lambda 2$ of the excitation light is 1268.8 nm, and terahertz waves having a frequency of 2.6 THz have been generated from the terahertz wave generation element 32A. FIG. 17 illustrates one dimensional imaging results of intensities of terahertz waves that have been transmitted through the respective sample stages A and B, in a case in which the wavelength λ2 of the excitation light is 1278 nm, and terahertz waves having a frequency of 4.3 THz have been generated from the terahertz wave generation element 32A. Moreover, the shielding rates of terahertz waves are listed below for the sample stages A and B at each frequency of the generated terahertz waves.

TABLE 1

| Generated THz wave | | Sample | THz wave intensity | | Shielding |
|---|---|---|---|---|---|
| Frequency | Wavelength | stage | No silver wire | Silver wire | rate |
| 2.6 THz | 115 μm | A | 39.7 mV | 1.5 mV | 96.3% |
|  |  | B | 39.9 mV | 19.5 mV | 51.1% |
| 4.3 THz | 70 μm | A | 106.9 mV | 3.8 mV | 96.5% |
|  |  | B | 97.3 mV | 41.2 mV | 57.6% |

The terahertz wave intensities for "no silver wire" in the table above are average values at set locations in ranges where the terahertz wave intensity is not shielded in the imaging results illustrated in FIG. 16 and FIG. 17. The terahertz wave intensities for "silver wire" are minimum values in the imaging results illustrated in FIG. 16 and FIG. 17. Moreover, the shielding rate is given by:

shielding rate=(THz without silver wire−THz with silver wire)/THz without silver wire Note that "THz" in the above equation indicates the terahertz wave intensity. Moreover, the noise floor of the detected terahertz waves is 6.6 mV.

As illustrated in FIG. 16 and FIG. 17 and the above table, although shielding of the terahertz waves to the noise floor or below was achieved with the sample stage A, the shielding rate of the terahertz waves decreased in the sample stage B. A more detailed comparative verification follows.

Although the wavelength of the generated terahertz waves was 115 μm when terahertz waves were generated with a frequency of 2.6 THz, the beam diameter of the terahertz waves could not be condensed to the wavelength of 115 μm or lower due to the diffraction limit when the generated terahertz waves were condensed and made incident to the sample disposed on the sample stage B. Namely, in the case of the sample stage B, the silver wire the shielding rate is 51.1% for a 75 μm diameter of silver wire since the beam diameter of the terahertz waves incident to the sample are above 115 μm, and a high shielding rate could not be achieved.

On the other hand, in the case of the sample stage A, terahertz waves having a beam diameter substantially the same as the 65 μm beam diameter of the excitation light incident to the terahertz wave generation element 32A is incident to the sample since the terahertz wave generation element 32A and the finely engineered structure 32B holding the sample were in close contact with each other. Namely, in the case of the sample stage A, a high shielding rate of 96.3% is obtained since the beam diameter of the terahertz waves incident to the sample is 65 μm for a 75 μm diameter of silver wire. Moreover, in the case of the sample stage A, the terahertz wave intensities with the silver wire were below the noise floor of 6.6 mV, and complete shielding of the terahertz waves was achieved.

Moreover, when terahertz waves were generated with a frequency of 4.3 THz, the wavelength of the generated terahertz waves was 70 μm, although, due to being shorter than the 75 μm diameter of the silver wire, the shielding rate at the sample stage B was raised at 57.6%, complete shielding of the terahertz waves was not achieved.

On the other hand, in the case of the sample stage A, similarly to when terahertz waves were generated with a frequency of 2.6 THz, the terahertz wave intensity with silver wire was below the noise floor, and complete shielding of terahertz waves was achieved.

Thus, the case of the sample stage A, namely, the case in which the terahertz wave generation element 32A and the structure that holds the sample are in close contact with each other, as in technology disclosed herein, enables the acquisition of optical characteristics of terahertz waves at a resolution exceeding the diffraction limit, and the acquisition of images from imaging.

What is claimed is:

1. A terahertz wave measuring device comprising:
   a terahertz wave generation element that generates a terahertz wave by difference frequency generation based on excitation light that is incident to the terahertz wave generation element, the excitation light including a plurality of different wavelength components and being condensed so as to have a beam diameter of a predetermined size;
   a structural body through which the terahertz wave is transmitted; and
   a detector that detects an intensity of the terahertz wave that has been transmitted through the structural body,
   wherein the structural body includes a sample holder of a predetermined width that holds a sample, and the structural body is disposed so as to be in close contact with or to be joined to the terahertz wave generation element,
   wherein the predetermined size of the beam diameter of the excitation light is smaller than the wavelength of the terahertz wave and shorter than the width of the sample holder, and
   wherein a beam diameter of the terahertz wave, which is irradiated to the structural body, is smaller than the wavelength of the terahertz wave.

2. The terahertz wave measuring device of claim 1, further comprising:
   a moving section that moves a light path of the excitation light, or moves the structural body, such that an incident position of the excitation light is moved in one dimension or in two dimensions with respect to the terahertz wave generation element,
   wherein the detector detects the intensity of the terahertz wave according to the incident position of the excitation light with respect to the terahertz wave generation element.

3. The terahertz wave measuring device of claim 1, wherein the terahertz wave generation element is a non-linear optical crystal that achieves phase matching in difference frequency generation.

4. The terahertz wave measuring device of claim 3, wherein the non-linear optical crystal is an organic non-linear optical crystal that is a DAST crystal, a DASC crystal, or an OH1 crystal.

5. A terahertz wave measuring method comprising:
   condensing excitation light including light of a plurality of different wavelength components so as to have a beam diameter of a predetermined size;

having the condensed excitation light be incident to a terahertz wave generation element so as to generate a terahertz wave by difference frequency generation based on the condensed excitation light;

transmitting the terahertz wave through a structural body that includes a sample holder of a predetermined width that holds a sample, the structural body being disposed so as to be in close contact with or being joined to the terahertz wave generation element; and detecting an intensity of the terahertz wave that has been transmitted through the structural body, wherein the predetermined size of the beam diameter of the excitation light is smaller than the wavelength of the terahertz wave and shorter than the width of the sample holder, and wherein a beam diameter of the terahertz wave, which is irradiated to the structural body, is smaller than the wavelength of the terahertz wave.

6. The terahertz wave measurement method of claim 5, further comprising:

comparing an intensity of the terahertz wave detected for a sample to be measured against an intensity of the terahertz wave detected in advance for a known sample of known concentration; and measuring the concentration of the sample to be measured.

7. The terahertz wave measurement method of claim 5, further comprising:

comparing an intensity of the terahertz wave detected for a sample to be measured against respective intensities of terahertz waves detected in advance for known samples; and identifying the sample to be measured.

8. A terahertz wave measuring rig comprising:

a terahertz wave generation element that generates a terahertz wave by difference frequency generation based on excitation light, including light of a plurality of different wavelength components that is condensed so as to have a beam diameter of a predetermined size, being incident to the terahertz wave generation element; and a structural body through which the terahertz wave is transmitted, wherein the structural body includes a sample holder of a predetermined width that holds a sample, and the structural body is disposed so as to be in close contact with or to be joined to the terahertz wave generation element, wherein the predetermined size of the beam diameter of the excitation light is smaller than the wavelength of the terahertz wave and shorter than the width of the sample holder, and wherein a beam diameter of the terahertz wave, which is irradiated to the structural body, is smaller than the wavelength of the terahertz wave.

* * * * *